US007942882B2

(12) United States Patent
Tornier et al.

(10) Patent No.: US 7,942,882 B2
(45) Date of Patent: May 17, 2011

(54) ANCILLARY TOOL FOR FITTING A HUMERAL COMPONENT OF AN ELBOW PROSTHESIS

(75) Inventors: Alain Tornier, Saint Ismier (FR); Shawn O'Driscoll, Rochester, MN (US); Graham King, London (CA); Ken Yamaguchi, St. Louis, MO (US); Yves Alain Ratron, Grenoble (FR); Bruno Scialom, Gieres (FR)

(73) Assignee: Tornier SAS, Saint Ismier (FR)

( * ) Notice: Subject to any disclaimer, the term of this patent is extended or adjusted under 35 U.S.C. 154(b) by 1754 days.

(21) Appl. No.: 10/189,630

(22) Filed: Jul. 8, 2002

(65) Prior Publication Data

US 2003/0009171 A1 Jan. 9, 2003

Related U.S. Application Data

(60) Provisional application No. 60/303,322, filed on Jul. 9, 2001.

(51) Int. Cl.
*A61B 17/58* (2006.01)
*A61B 17/60* (2006.01)
*A61F 2/00* (2006.01)

(52) U.S. Cl. .................................. 606/96; 606/86 R (58) Field of Classification Search ............ 606/90, 606/96, 99, 79, 86–89; 623/20.11–20.36
See application file for complete search history.

(56) References Cited

U.S. PATENT DOCUMENTS

| 4,131,956 | A | * | 1/1979 | Treace | 623/20.11 |
| 4,159,716 | A | * | 7/1979 | Borchers | 606/96 |
| 4,235,428 | A | * | 11/1980 | Davis | 606/96 |
| 4,242,758 | A | * | 1/1981 | Amis et al. | 623/20.11 |
| 4,257,411 | A | * | 3/1981 | Cho | 606/96 |
| 4,292,964 | A | * | 10/1981 | Ulrich | 606/80 |
| 4,718,414 | A | | 1/1988 | Saunders | |
| 5,171,289 | A | | 12/1992 | Tornier | |

(Continued)

FOREIGN PATENT DOCUMENTS

EP          0132284       1/1985

OTHER PUBLICATIONS

Rochetin, U.S. Appl. No. 11/194,452, entitled "Patellar Retractor and Method of Surgical Procedure on Knee," filed Aug. 2, 2005.

(Continued)

*Primary Examiner* — Thomas C Barrett
*Assistant Examiner* — Andrew Yang
(74) *Attorney, Agent, or Firm* — Faegre & Benson LLP (57) ABSTRACT

An ancillary tool for fitting a humeral component of a total or partial elbow prosthesis, comprising a guiding tool (30) for boring a humeral trochlea (T) along a geometric axis (X-X') of bend of a joint to be equipped with said prosthesis. The guiding tool (30) includes a stirrup element (31) and means (32$b$, 33$b$) for securing said stirrup element on the humeral trochlea (T) so that said guiding tool defines a guiding zone that is aligned in the geometric axis of bend for the introduction (F$_1$) of a drill (40), a punch or the like, in the humeral trochlea (T) along said geometric axis of bend. This ancillary tool also comprises at least one stepped template (70$_1$, 70$_2$, 70$_3$) for determining an anterior offset of said geometric axis of bend (X-X') with respect to a humeral diaphyseal axis (Y-Y').

20 Claims, 8 Drawing Sheets

U.S. PATENT DOCUMENTS

| | | |
|---|---|---|
| 5,314,485 A | 5/1994 | Judet |
| 5,326,359 A | 7/1994 | Oudard |
| 5,358,526 A | 10/1994 | Tornier |
| 5,405,399 A | 4/1995 | Tornier |
| 5,429,639 A | 7/1995 | Judet |
| 5,458,650 A | 10/1995 | Carret et al. |
| 5,474,559 A * | 12/1995 | Bertin et al. .................... 606/89 |
| 5,505,731 A | 4/1996 | Tornier |
| 5,514,139 A * | 5/1996 | Goldstein et al. ............... 606/79 |
| 5,591,168 A | 1/1997 | Judet et al. |
| 5,662,651 A | 9/1997 | Tornier et al. |
| 5,676,702 A | 10/1997 | Ratron |
| 5,702,447 A | 12/1997 | Walch et al. |
| 5,702,457 A | 12/1997 | Walch et al. |
| 5,702,478 A | 12/1997 | Tornier |
| 5,766,256 A | 6/1998 | Oudard et al. |
| 5,824,106 A | 10/1998 | Fournol |
| 5,879,395 A | 3/1999 | Tornier et al. |
| 6,162,254 A | 12/2000 | Timoteo |
| 6,165,224 A | 12/2000 | Tornier |
| 6,168,629 B1 | 1/2001 | Timoteo |
| 6,171,341 B1 | 1/2001 | Boileau et al. |
| 6,183,519 B1 | 2/2001 | Bonnin et al. |
| 6,206,925 B1 | 3/2001 | Tornier |
| 6,299,646 B1 | 10/2001 | Chambat et al. |
| 6,328,758 B1 | 12/2001 | Tornier et al. |
| 6,334,874 B1 | 1/2002 | Tornier et al. |
| 6,379,387 B1 | 4/2002 | Tornier |
| 6,454,809 B1 | 9/2002 | Tornier |
| 6,488,712 B1 | 12/2002 | Tornier et al. |
| 6,540,770 B1 | 4/2003 | Tornier et al. |
| 6,582,469 B1 | 6/2003 | Tornier |
| 6,599,295 B1 | 7/2003 | Tornier et al. |
| 6,626,946 B1 | 9/2003 | Walch et al. |
| 6,761,740 B2 | 7/2004 | Tornier |
| 6,767,368 B2 | 7/2004 | Tornier |
| 6,802,864 B2 | 10/2004 | Tornier |
| 6,824,567 B2 | 11/2004 | Tornier et al. |
| 6,890,357 B2 | 5/2005 | Tornier |
| 6,969,406 B2 | 11/2005 | Tornier |
| 7,033,396 B2 | 4/2006 | Tornier |
| 2003/0009170 A1 | 1/2003 | Tornier |
| 2003/0028198 A1 | 2/2003 | Tornier et al. |
| 2004/0134821 A1 | 7/2004 | Tornier |
| 2004/0210220 A1 | 10/2004 | Tornier |
| 2004/0215200 A1 | 10/2004 | Tornier et al. |
| 2004/0230197 A1 | 11/2004 | Tornier et al. |
| 2005/0049709 A1 | 3/2005 | Tornier |
| 2005/0055102 A1 | 3/2005 | Tornier et al. |
| 2005/0165490 A1 | 7/2005 | Tornier |
| 2005/0203536 A1 | 9/2005 | Laffargue et al. |
| 2005/0278030 A1 | 12/2005 | Tornier et al. |
| 2005/0278031 A1 | 12/2005 | Tornier et al. |
| 2005/0278032 A1 | 12/2005 | Tornier et al. |
| 2005/0278033 A1 | 12/2005 | Tornier et al. |
| 2005/0288791 A1 | 12/2005 | Tornier et al. |
| 2006/0015185 A1 | 1/2006 | Chambat et al. |
| 2006/0173457 A1 | 8/2006 | Tornier |
| 2006/0235538 A1 | 10/2006 | Rochetin et al. |

OTHER PUBLICATIONS

Rochetin et al., U.S. Appl. No. 11/401,415, entitled "Surgical Apparatus for Implantation of a Partial or Total," filed Apr. 11, 2006.

Rochetin, U.S. Appl. No. 11/670,274, entitled "Offset Stem Tibial Implantation," filed Feb. 1, 2007.

Ratron et al., U.S. Appl. No. 11/626,735, entitled "Surgical Instrumentation Kit for Inserting an Ankle Prothesis," filed Jan. 24, 2007.

* cited by examiner

ANCILLARY TOOL FOR FITTING A HUMERAL COMPONENT OF AN ELBOW PROSTHESIS

CROSS REFERENCE TO RELATED APPLICATION

This application claims the benefit of U.S. Provisional Patent Application Ser. No. 60/303,322 filed on Jul. 9, 2002 by the same inventor, Alain Tornier.

FIELD OF THE INVENTION

The invention relates to an ancillary tool for fitting a humeral component of a total or partial elbow prosthesis.

BACKGROUND OF THE INVENTION

An elbow prosthesis, such as known from EP-A-1 051 954, comprises a humeral component which must reproduce the anatomical trochlea by an artificial trochlea. The positioning of this artificial trochlea with respect to the joint is essential for the elbow thus fitted out to function well.

Up to the present time, surgeons implant the humeral component of an elbow prosthesis by assuming that the position of the axis of bend of the joint can be determined empirically from that of the medullary canal. Now, this is not strictly exact, resulting in defective positioning of the artificial trochlea with respect to the ulnar and radial articular surfaces with which it must cooperate, whether it be the anatomical surfaces or of prosthesis surfaces.

SUMMARY OF THE INVENTION

It is a particular object of the present invention to overcome these drawbacks by proposing an ancillary fitting tool which allows a precise positioning of the artificial trochlea and thus improves the functional conditions of the elbow thus fitted out.

In this state of mind, the invention relates to an ancillary tool of the afore-mentioned type which comprises a guiding tool for boring the humeral trochlea along the geometric axis of bend of the joint to be fitted out, this tool comprising a stirrup element adapted to be immobilized on the trochlea, while the tool defines a guiding zone for the introduction of a drill, a punch or the like in the trochlea, along the axis of bend of the joint.

With the invention, the surgeon, before proceeding with a resection of the lower end of the humerus, can determine with precision the axis of bend of the joint and, by means of the bore made by the guiding tool, he/she can position a pin which then serves as physical reference axis for the subsequent measurements and the positioning of the artificial humeral component.

According to advantageous but non-obligatory aspects of the invention, this ancillary tool incorporates one or more of the following characteristics:

The aforementioned tool comprises a hollow screw adapted to exert on the trochlea an effort for immobilization of the tool, in cooperation with a part of the stirrup element. In that case, the aforementioned part of the stirrup is advantageously provided with pins for immobilization with respect to the trochlea and with a notch for engagement of the epitrochlea.

It comprises a template for positioning the guiding tool with respect to the outer face of the trochlea. This template makes it possible to determine the zone of abutment of a hollow screw on the condyle, i.e. the point of introduction of the drill or of the punch in the anatomical epicondyle.

It comprises a pin adapted to be partially introduced in the humeral medullary canal, substantially along the diaphyseal axis, and at least one stepped template for determining the anterior offset of the axis of bend with respect to the diaphyseal axis, this template being adapted to slide along the afore-mentioned pin. This template may be in one piece, provided with a central bore whose diameter corresponds to the diameter of that part of the afore-mentioned pin which projects from the medullary canal, this piece being equipped with three annular surfaces centered on this bore and capable of coming into abutment against a pin in place in the trochlea, along the axis of bend. The template may be provided to include marks corresponding to pre-established references of values of the anterior offset, and to be in several sizes corresponding respectively to predetermined sizes of standard trochleas.

A plurality of trial trochleas can be provided, which are adapted to be used for determining the approximate size of the anatomical trochlea of the joint to be fitted out. Such trial trochleas make it possible to determine which stepped template must be used for determining the aforementioned anterior offset and/or which positioning template must be used for positioning the guiding tool.

It comprises a guiding tool for cutting out the humerus, this tool including a support adapted to be positioned with respect to a pin in place in the trochlea along the aforementioned axis of bend and a template adapted to be mounted on the support, defining at least one zone for guiding a cut-out tool.

The invention allows the fitting of a humeral component of an elbow prosthesis in accordance with a method which includes steps consisting in determining the geometric position of the axis of bend of the joint to be fitted out with respect to the humeral trochlea, in boring this trochlea along that axis and in inserting a first pin in this trochlea along that axis. Due to this method, the artificial trochlea may be positioned with precision and may interact with the complementary articular surfaces under optimal conditions.

Depending on the circumstances, this method may include additional steps consisting in partially introducing a second pin in the humeral medullary canal, substantially along the diaphyseal axis, and in measuring the anterior offset of the axis of bend with respect to the diaphyseal axis, by sliding a stepped template along the second pin until it comes into contact with the first.

According to another aspect of this method, it is possible to select from a set of boring trochleas, that trochlea whose geometry is the closest to the anatomical trochlea, and to select the stepped template in function of the boring trochlea already selected.

Furthermore, it is possible to provide additional steps consisting in positioning, on the first pin in place in the trochlea along the axis of bend, a guiding tool for cutting out the humerus, and in cutting out the humerus along a profile determined by this guiding tool.

Finally, it may be provided to determine the angle between the axis of bend and the projection on this axis of the humeral diaphyseal axis.

BRIEF DESCRIPTION OF THE DRAWINGS

The invention will be more readily understood and other advantages thereof will appear more clearly in the light of the following description of a form of embodiment of an ancillary fitting tool in accordance with its principle, and of its implementation, given solely by way of example and made with reference to the accompanying drawings, in which.

DESCRIPTION OF THE PREFERRED EMBODIMENT

The lower end of the humerus H shown in the Figures comprises an anatomical trochlea T constituting the lower articular surface S of the humerus. This surface S is partially cylindrical and centered on an imaginary axis X-X' which constitutes the geometric axis of bend of the elbow joint.

Figure 1:
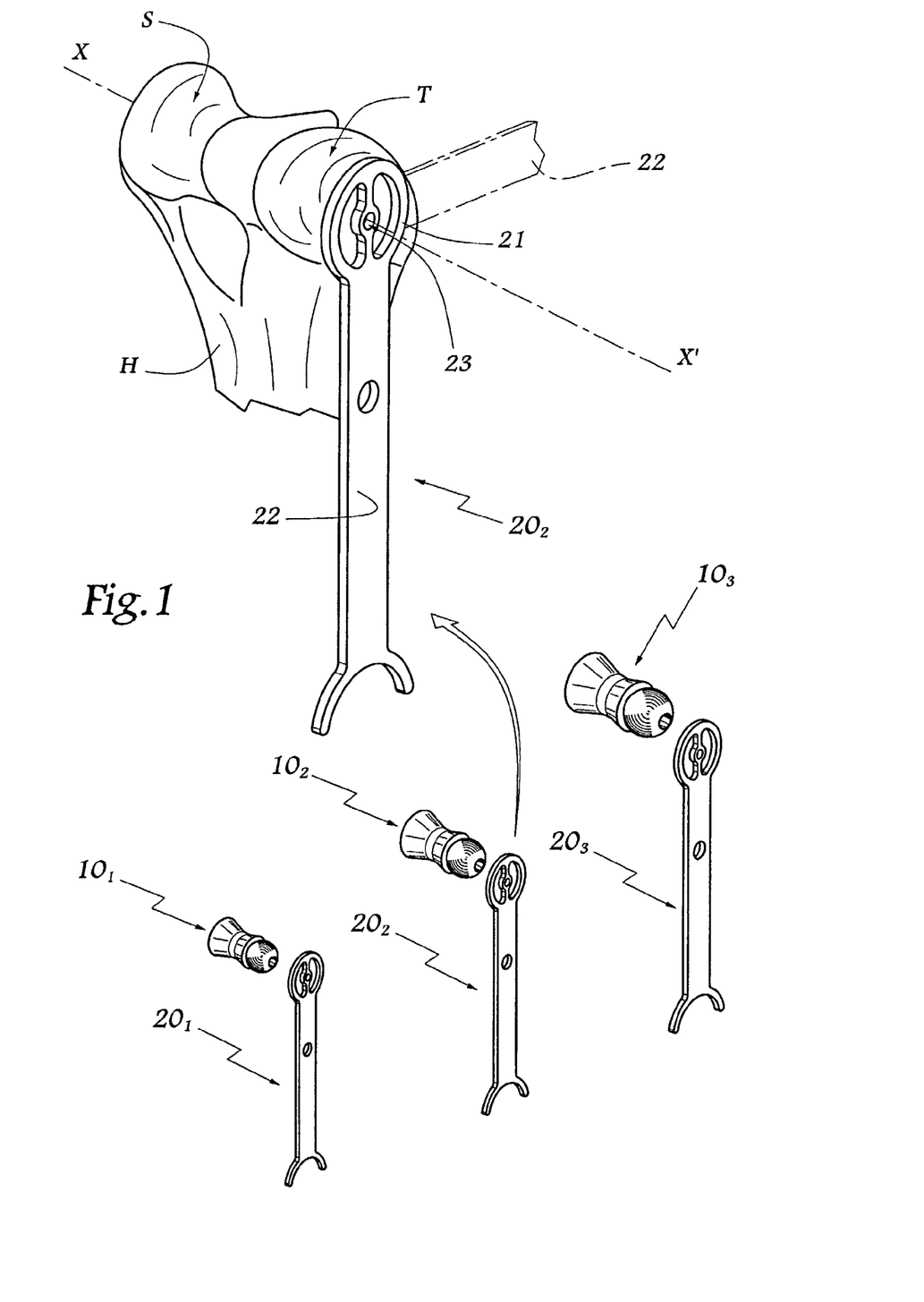
FIG. 1 is a view in perspective of the lower end of a humerus, during a first step of fitting a humeral component thanks to an ancillary tool according to the invention, associated elements being shown on a smaller scale.

In a first step of use of the ancillary tool of the invention, the anatomical trochlea T is compared with three trial trochleas $10_1$, $10_2$, $10_3$ of different sizes. For example, the size of trochlea $10_1$ is smaller than that of trochlea $10_2$ which is itself smaller than trochlea $10_3$. Further to this comparison, one of the three trial trochleas is selected, for example trochlea $10_2$, as being the one geometrically closest to the anatomical trochlea T.

In function of the trial trochlea selected, in the example of trochlea $10_2$, a positioning template $20_2$ is selected from a set of three templates $20_1$, $20_2$, $20_3$ corresponding respectively to trochleas $10_1$ to $10_3$. The template 20 may also be selected by placing its end 21 on the humeral condyle and by verifying that it adequately matches the profile of this condyle.

To render the drawing clearer, elements $10_1$ to $10_3$ and $20_1$ to $20_3$ have been shown, in the lower part of FIG. 1, on a smaller scale than the humerus H and the template $20_2$ in the upper part.

The template $20_2$ selected is then placed on the side of the humerus H so that its end 21 of rounded form is in abutment on the outer condyle of the humerus. In practice, the handle 22 of the template $20_2$ may be disposed parallel to the humerus H, as represented in solid lines in FIG. 1, or perpendicularly thereto, as represented in dashed and dotted lines.

The end 21 of the template $20_2$ is positioned so that the center of the trochlea T through which axis X-X' passes can be marked with acceptable precision. This end 21 is provided with a central bore 23 in which may be inserted a tip for marking the condyle in question. The template $20_2$ therefore makes it possible to mark the trace of axis X-X' on the condyle of the trochlea T.

Figure 2:
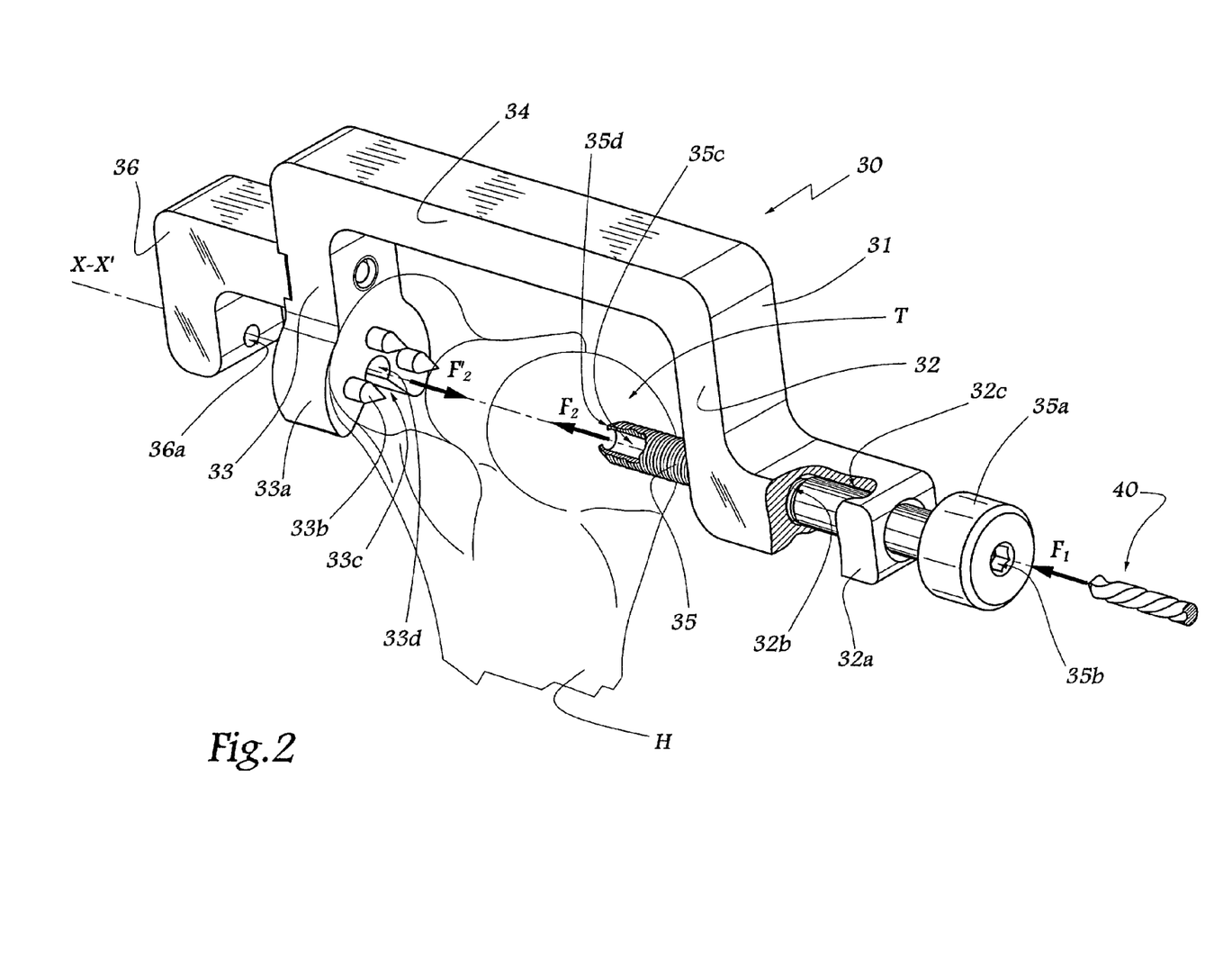
FIG. 2 is a view similar to FIG. 1, with parts torn away, during a second step.

It is then possible to use a guiding tool 30 for piercing the trochlea Y along axis X-X'. This tool 30 comprises a substantially U-shaped stirrup element 31 which comprises a first arm 32 and a second arm 33 connected by a base 34. The end 32a of the arm 32 is substantially parallel to the base 34 and is equipped with a tapping 32b extended by a centering recess 32c for guiding and receiving a screw 35 of which the head 35a is provided with a polygonal orifice 35b allowing it to be driven by a suitable male wrench.

The screw 35 is hollow, in that it is provided with a longitudinal channel 35c which extends over the whole of its length and which is visible in the part torn away in FIG. 2.

The second arm 33 of the stirrup element 31 terminates in an end 33a provided with three pins 33b and with a notch 33c intended to receive the epitrochlea of the humerus H, which has been shown faintly in FIG. 2 in order to facilitate visualization of the tool 30.

An accessory arm 36 is added on the stirrup element 31 and extends from the arm 33 in a direction substantially parallel to the base 34, then in a direction substantially perpendicular to said base. The arm 36 is bored with an orifice 36a substantially aligned with an orifice 33d provided in the end 33a of the arm 33 and aligned precisely with the channel 35c of the screw 35 when the latter is in place in the tapping 32b. The orifice 36a allows a sight of the axis of bend by the inner face of the humerus, when this is necessary.

The tool 30 is positioned on the humerus H by aiming the front end 35d of the screw 35 on the mark made using the template $20_1$, $20_2$ or $20_3$ and by arranging the notch 33c around the epitrochlea of the humerus H. In this position, the axis common to the orifices 36a, 33d and to the channel 35c is substantially aligned with the axis of bend X-X', as defined by the trochlea T.

It is then possible to bore the trochlea T using a drill 40 traversing the screw 35, the end 33a and the orifice 36a. Arrow $F_1$ represents the direction of introduction of the drill 40 in the channel 35c, the orifice 33d and the orifice 36a.

In place of the drill 40, a punch may be used, or any other tool suitable for boring the trochlea T along axis X-X'. The drill 40 may also be introduced through the orifice 36a, depending on what the operating surgeon chooses.

It will be noted that the tool 30 may be firmly immobilized with respect to the humerus by the cooperation of the screw 35 and the pins 33 which exert an effort $F_2$, $F'_2$ of compression on the humerus H, in a direction substantially parallel to axis X-X'.

Figure 3:
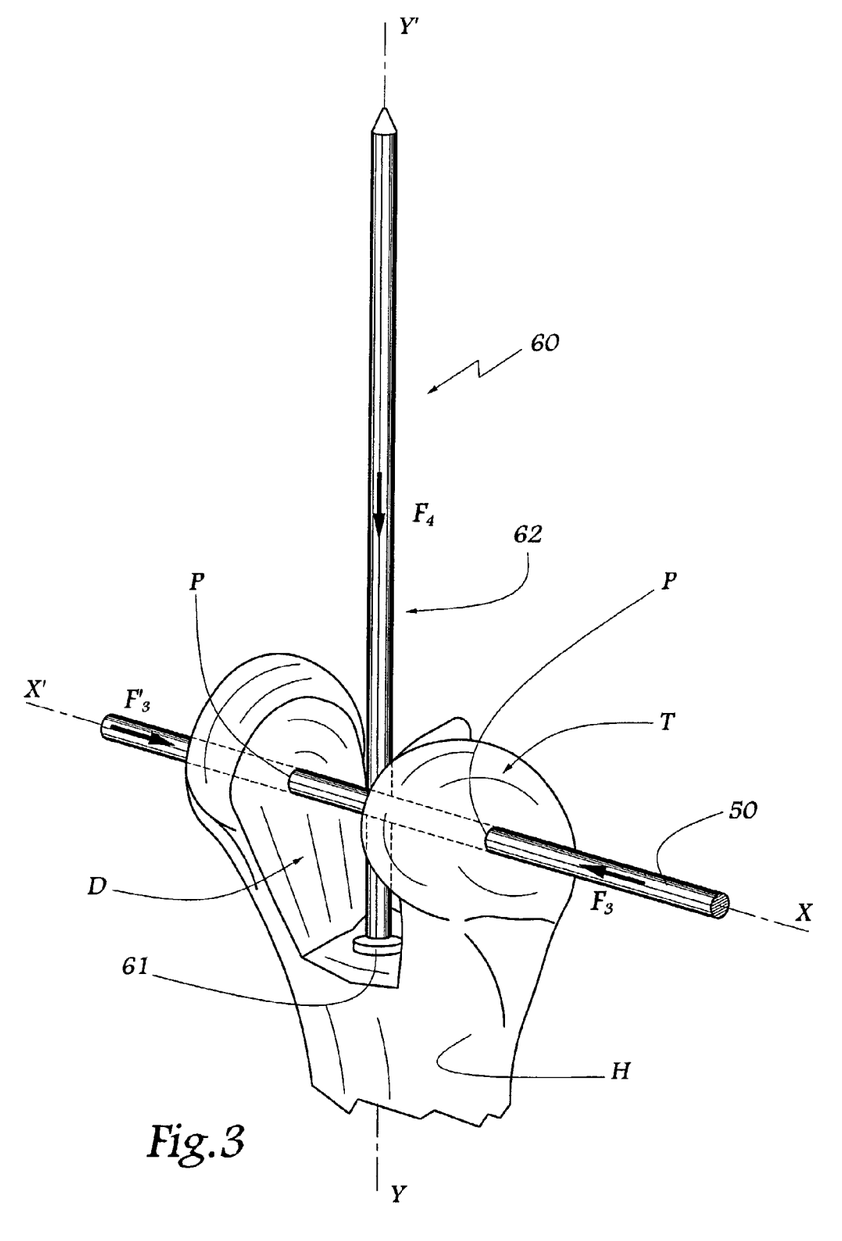
FIG. 3 is a view similar to FIG. 1 during a third step.

When said boring has been effected, it is possible to withdraw the tool 30 by unscrewing the screw 35, then to make in the humerus H a cut-out D for access to the medullary canal of the humerus, such cut-out being visible in FIG. 3.

It is then possible to insert in the bore P made by the drill 40, a pin 50 which then becomes the physical materialization of the geometric axis X-X'. Arrows $F_3$ and $F'_3$ represent the directions of introduction of the pin 50 in the bore P, along axis X-X'. There may also be inserted in the medullary canal of the humerus H a stepped pin 60 comprising a first section 61 of relatively large diameter, for example equal to 6 mm, and a second section 62 of smaller diameter, for example of the order of 3 mm. It may be assumed that the pin 60 extends substantially along the diaphyseal axis Y-Y' of the humerus. Arrow $F_4$ represents the direction of introduction of the pin 60 in the medullary canal.

The anterior offset d between axes X-X' and Y-Y' should then be determined at least approximately. This offset, sometimes called "anterior offset", corresponds to the distance between axes X-X' and Y-Y' in a direction perpendicular to these two axes.

It is essential to know the value of this offset in order to select an artificial trochlea of which the central axis will be able to be correctly positioned with respect to the diaphyseal axis of the humerus. Indeed, it is possible to provide different artificial trochleas, with axes positioned differently, as disclosed, for example, in EP-A-1 051 954.

Figure 4:
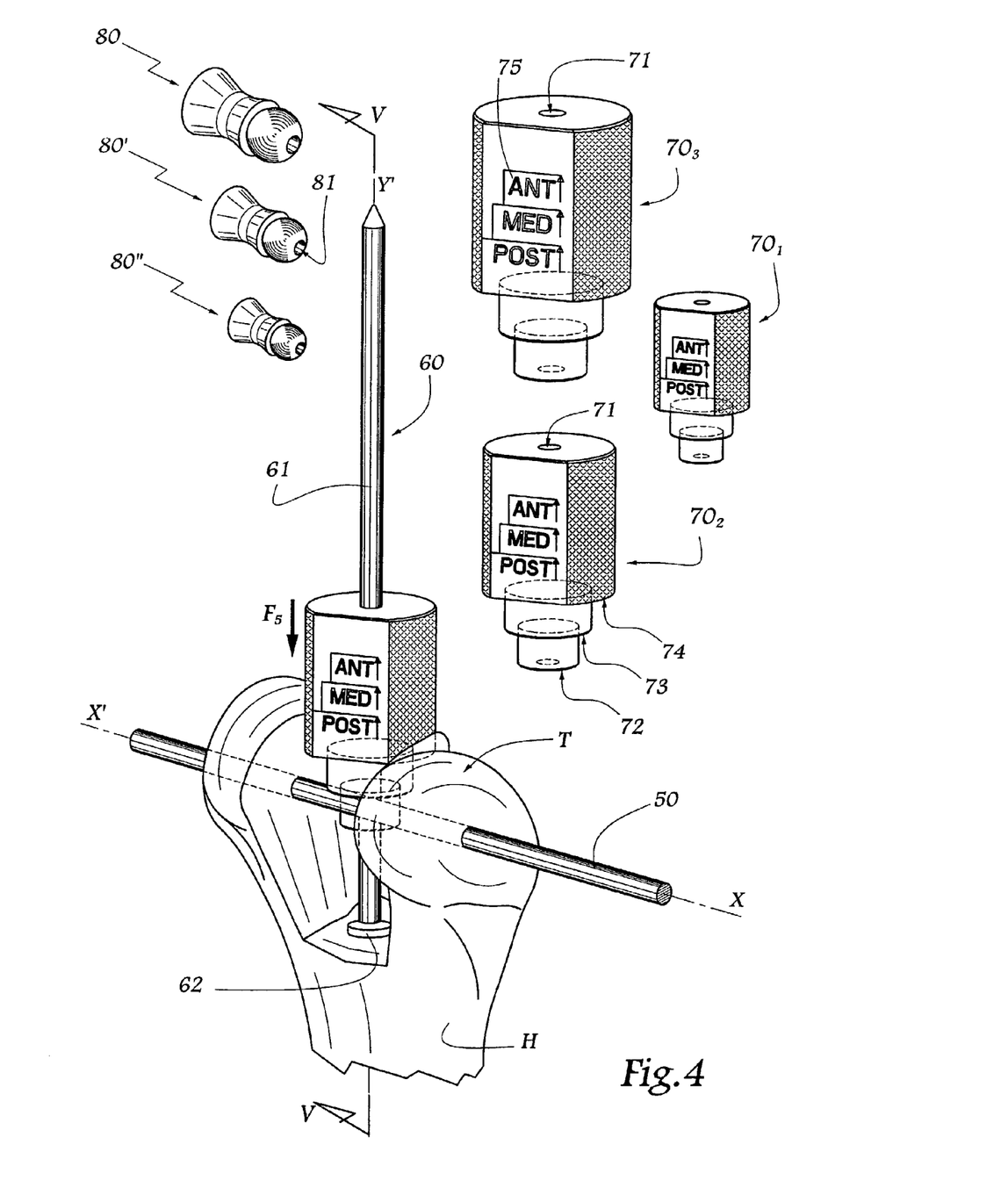
FIG. 4 is a view similar to FIG. 1 during a fourth step.

In order to proceed with the determination of the offset d, templates $70_1$, $70_2$, $70_3$ of stepped shape are used. More precisely, a template is selected as a function of the trial trochlea previously selected, trochlea $10_2$ in the example described. In that case, the template $70_2$ of intermediate size is selected and it is made to slide around the pin 60, as represented by arrow $F_5$. The templates $70_1$, $70_2$ and $70_3$ are each provided with a central bore 71 of diameter substantially equal to that of the section 62 of the arm 60, which allows them to slide on this pin without difficulty.

Figure 5:
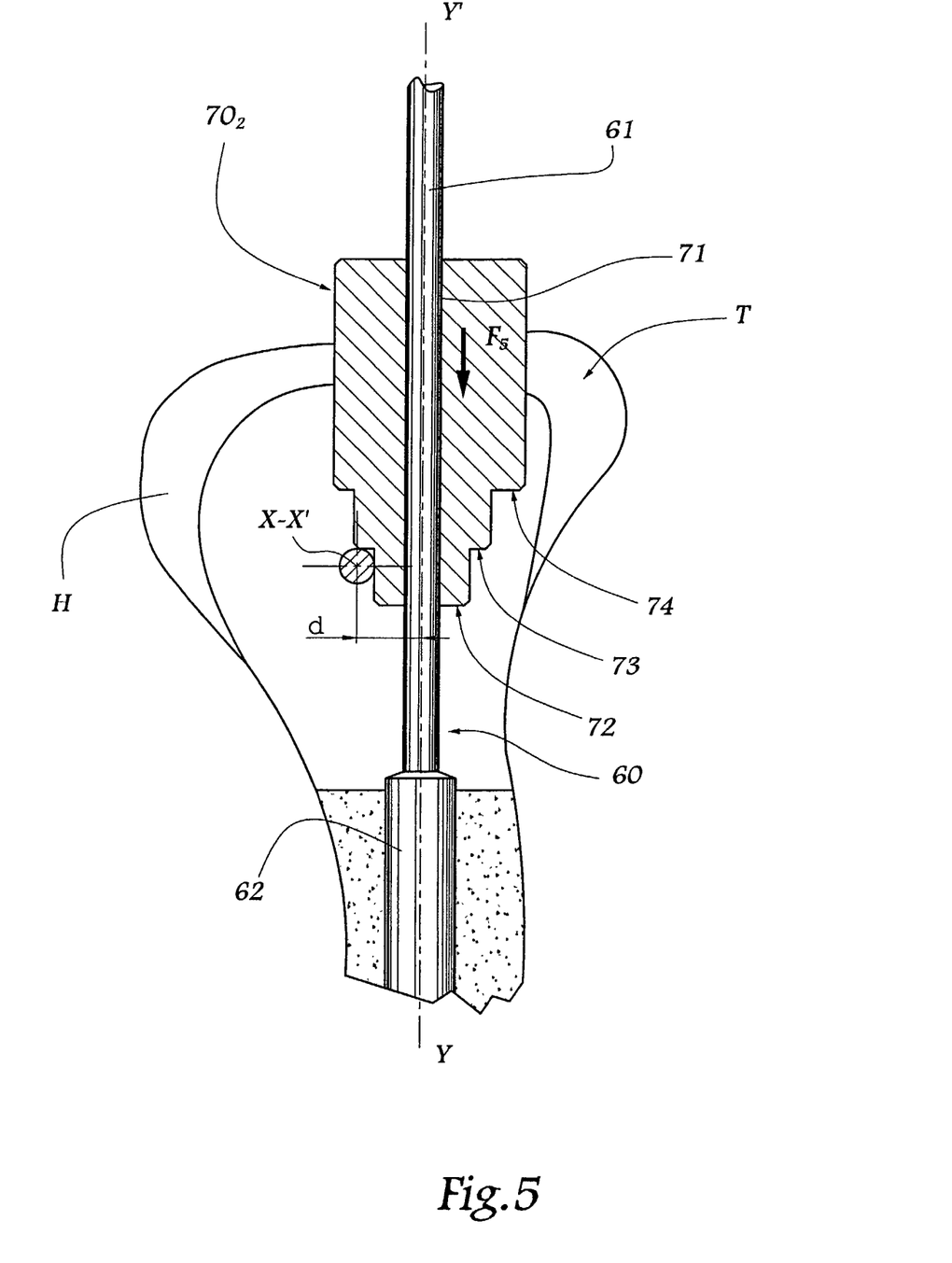
FIG. 5 is a section along line V-V in FIG. 4.

The template $70_2$ is provided with three annular surfaces 72, 73 and 74 with increasing diameters and which are each capable of bearing against the pin 50 in the configuration of FIGS. 4 and 5.

The templates $70_1$ and $70_2$ present substantially the same geometry, with stepped annular surfaces adapted to bear against the pin 50.

Each template $70_1$, $70_2$, $70_3$ bears markings 75 allowing the approximate value of the offset d to be immediately recognized, in the following manner:

ANT means "anterior", i.e. the anterior offset is great.
MED means "median", i.e. the anterior offset is medium.
POST means "posterior", i.e. the anterior offset is slight.

In this way, as a function of the surface 72, 73 or 74 bearing against the pin 50, the surgeon knows whether the offset d is to be considered as great, medium or slight, for the subsequent operation.

The fact of marking which surface 72, 73 or 74 of the template $70_2$ comes into contact with the pin 50 gives a good idea as to the value of the offset d and enables the artificial trochlea having to equip humerus H to be selected accordingly. The different artificial trochleas 80, 80' and 80" shown in FIG. 4 are in effect characterized by the positioning of their central bore 81 with respect to their outer surfaces, this central bore allowing them to be mounted on an element anchored in the humerus, in accordance with the technical teaching of EP-A-1 051 954.

Thus, the use of template $70_2$ enables the surgeon to know which of the artificial trochleas 80, 80' or 80" he must use in order to equip the humerus H.

It will be understood that three or more than three artificial trochleas may be provided to correspond to each size of template $70_1$, $70_2$, $70_3$.

The number of templates is, of course, not limited to three and, in practice, depends on the number of trial prostheses $10_1$, $10_2$, $10_3$ provided.

Figure 6:
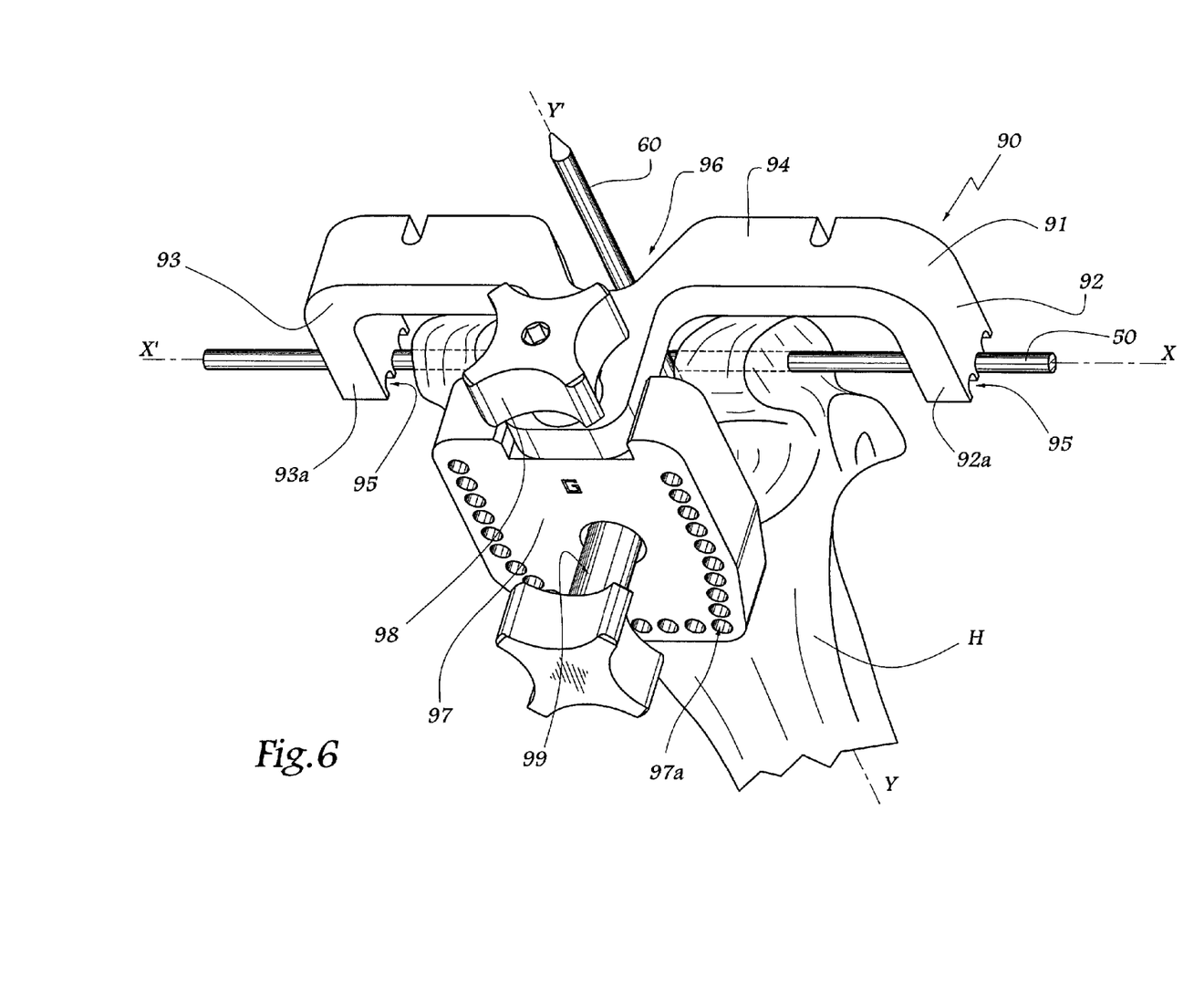
FIG. 6 is a view in perspective during a fifth step of using the ancillary tool.
Figure 7:
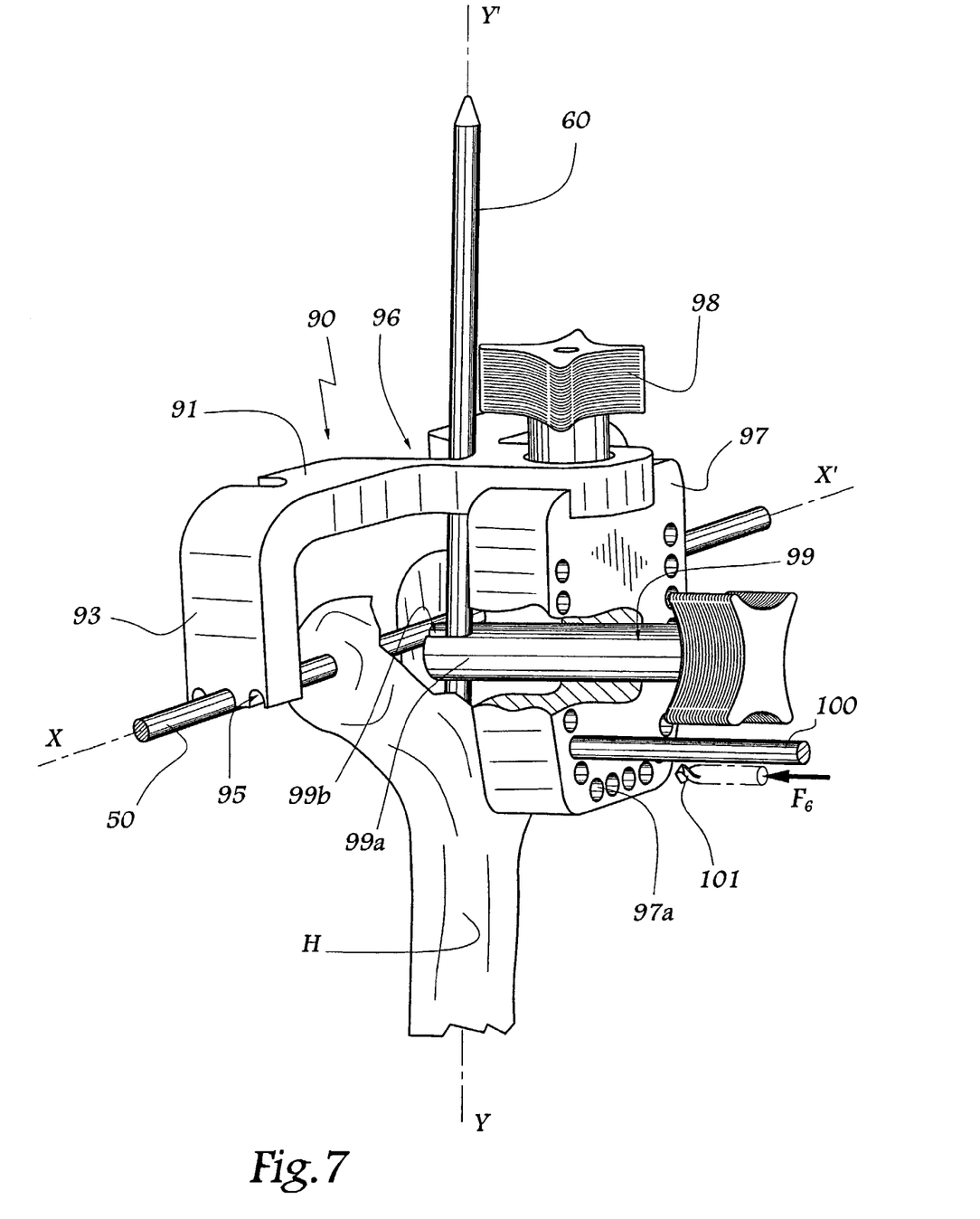
FIG. 7 is a view in perspective during a sixth step of using the ancillary tool.

When the offset d has been determined, a guiding tool 90 is used, which comprises a stirrup element 91 adapted to abut on the pin 50, as shown in FIGS. 6 and 7. This stirrup element comprises two arms 92 and 93 of which the respective ends 92a and 93a are provided with notches 95 for partially receiving the pin 50, this allowing the stirrup element 91 to be well immobilized on the pin 50.

The base 94 of the stirrup element 91 is provided with a cut-out 96 for passage of the pin 60.

A template 97 is provided to be immobilized on the stirrup element 91 with the aid of a locking screw 98. The template 97 bears a sliding spindle 99 provided, at its free end 99a, with a notch 99b, such that the end 99a may be arranged around the pin 60. This makes it possible to determine a satisfactory medio-lateral positioning of the template 97.

The template 97 may be mounted on the stirrup element 91 in two positions, corresponding respectively to its use for a left- or right-hand elbow joint. In this way, the same tool 90 can be used for the two types of elbows capable of being equipped.

The template 97 is provided with a plurality of bores 97a for passage of pins or drills making it possible to enlarge the cut-out D to the dimensions of the element having to be anchored in the humerus H.

As shown in FIG. 7, one or more pins 100 may be arranged in certain bores 97a, contributing to a good immobilization of the template 97 with respect to the humerus H, while the humerus H is bored by inserting a drill 101 successively in the other different bores 97a, as represented by arrow $F_6$. A punch or any other suitable tool may be used in place of the drill 101.

At the end of this operation, a cut-out D is obtained in the humerus H adapted for the positioning of an artificial humeral element 110.

Figure 8:
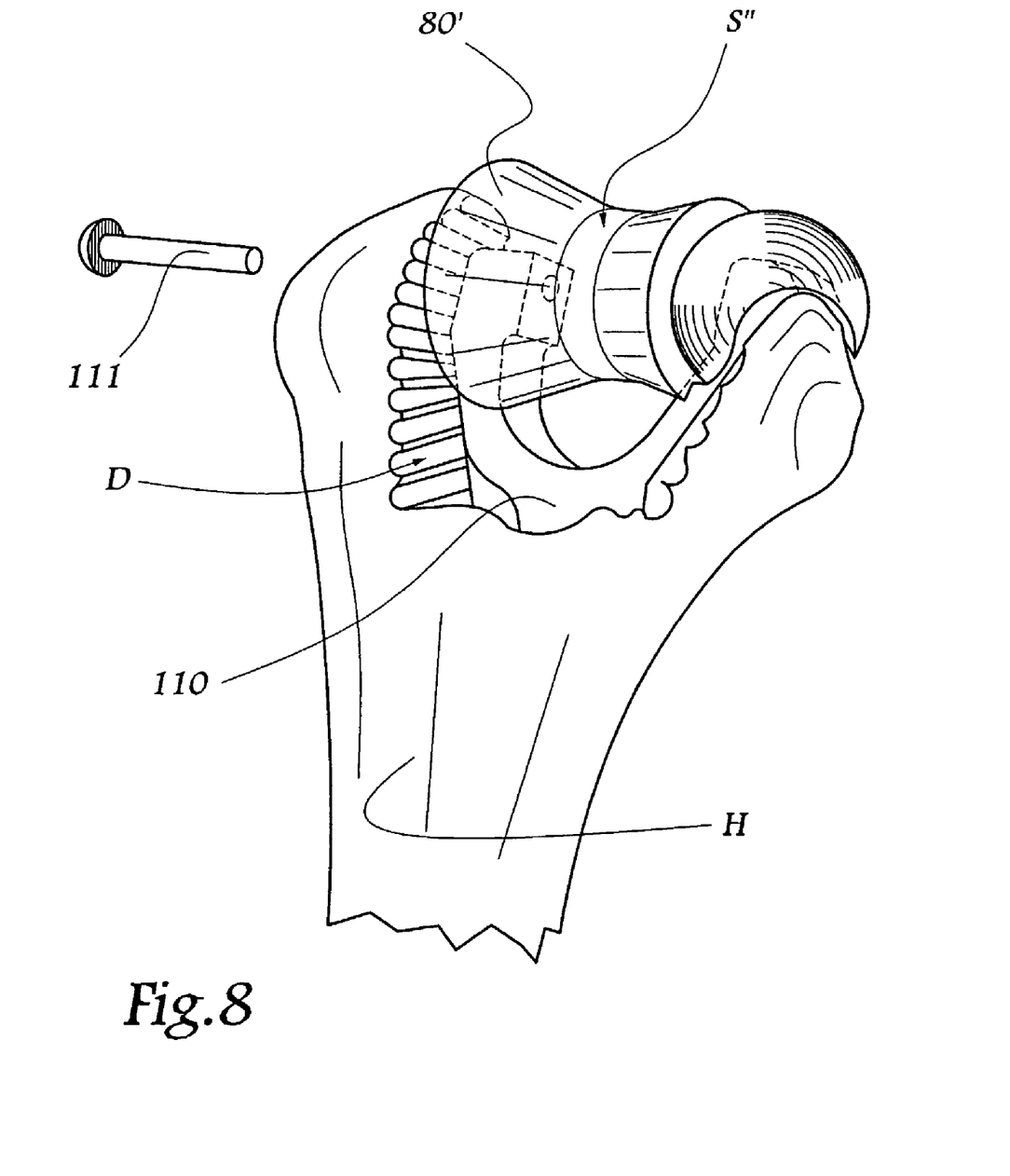
FIG. 8 is a view in perspective during the positioning of a trial artificial trochlea.

After enlargement of the cut-out D and before positioning of the element 110, the pins 50 and 60 are withdrawn and the bore previously used for the pin 60 is enlarged for positioning the element 110, as shown in FIG. 8. This element may receive a screw 111 for immobilization of the artificial trochlea 80, 80' or 80" selected thanks to the template $70_2$ used previously.

The outer articular surface S" of the trochlea 80' used is thus positioned precisely with respect to the anatomical surface S. In particular, the position of the geometric axis of the surface S" merges substantially with the geometric axis of bend X-X'.

When the tool 90 is in place on the pin 50, a protractor (not shown) may be mounted on the stirrup element 91, in order to measure the angle between the axis X-X' and its projection on the diaphyseal axis Y-Y'. The value of this angle may be used for determining the geometry of element 110.

In practice, the artificial trochleas 80, 80' and 80" are trial components, the definitive component being positioned at a subsequent stage of fitting the prosthesis, in particular after the possible fitting out of the ulna and/or of the radius.

The invention claimed is:

1. A system for implanting a prosthesis in a distal humeral trochlea of an elbow joint, the tool comprising:
    a first guide tool comprising a boring guide aligned to create a bore in the distal humeral trochlea along a geometric axis of bend of the elbow joint when the first guide tool is engaged with the distal humeral trochlea;
    a first pin insertable into a bore formed by the first guide tool in the distal humeral trochlea, the first pin providing a physical reference corresponding to the geometric axis of bend;
    a second pin insertable into a humeral medullary canal generally along a diaphyseal axis of a humerus and generally perpendicular to the first pin, the second pin providing a physical reference corresponding to the diaphyseal axis;
    at least one template adapted to measure an offset between the geometric axis of bend and the diaphyseal axis; and
    a first cutting template engaged with at least the first pin and oriented to cut the distal humeral trochlea generally perpendicular to the geometric axis of bend.

2. The system of claim 1 comprising a plurality of trial distal humeral trochlea adapted to evaluate features of at least a portion of an anatomical distal humeral trochlea in the elbow joint.

3. The system of claim 1 comprising a trial distal humeral trochlea selected from a plurality of trial distal humeral trochlea based on the offset between the geometric axis of bend and the diaphyseal axis.

4. The system of claim 1 comprising a positioning template adapted to determine a location of the geometric axis of bend.

5. The system of claim 1 wherein the first guide tool comprises a threaded member adapted to compressively engage the distal humeral trochlea, the threaded member comprising a longitudinal channel with a central axis adapted to align with the geometric axis of bend.

6. The system of claim 1 wherein the first guide tool comprises a notch shaped to engage an epitrochlea of a humerus and an orifice configured for alignment with the geometric axis of bend during engagement of the notch with the epitrochlea.

7. The system of claim 1 wherein the first guide tool comprises:
  first and second arms adapted to engage opposite sides of the distal humeral trochlea;
  a member coupled to the first arm adapted to compressively engage the distal humeral trochlea, the member comprising a longitudinal channel with a central axis adapted to align with the geometric axis of bend; and
  a notch in the second arm shaped to engage an epitrochlea of a humerus and an orifice configured for alignment with the geometric axis of bend during engagement of the notch with the epitrochlea.

8. The system of claim 1 wherein the first guide tool comprises first and second arms adapted to engage opposite sides of the distal humeral trochlea, wherein the first and second arms each include guide channels adapted to be arranged co-linear with the geometric axis of bend.

9. The system of claim 1 comprising a securing mechanism adapted to releasably secure the first guide tool to the distal humeral trochlea.

10. The system of claim 1 comprising a threaded member adapted to compressively engage the first guide tool with the distal humeral trochlea.

11. The system of claim 1 comprising a plurality of stepped templates, at least one of the stepped templates corresponding generally to at least one trial distal humeral trochlea.

12. The system of claim 1 comprising a stepped template, wherein the stepped template comprises markings corresponding to a value of anterior offset between the geometric axis of bend and the diaphyseal axis.

13. The system of claim 1 comprising a stepped template, wherein the stepped template comprises a central bore sized to permit engagement with the second pin.

14. The system of claim 1 comprising a stepped template, wherein the stepped template comprises a plurality of steps, each step corresponding to a different offset.

15. The system of claim 1 comprising a second guide tool adapted to engage with at least the first pin, the second guide tool adapted to prepare the distal humeral trochlea to receive an artificial trochlea.

16. The system of claim 1 comprising a second guide tool adapted to engage with at least the first pin, wherein the cutting template is attached to the second guide tool and is adapted to prepare the distal humeral trochlea to receive an artificial humeral element.

17. The system of claim 1 comprising a mechanism adapted to implant a prosthesis in either a left elbow joint or a right elbow joint.

18. The system of claim 1 comprising a member adapted to determining an angle between the geometric axis of bend and a projection of the geometric axis of bend on the diaphyseal axis.

19. A system for implanting a prosthesis in a distal humeral trochlea of an elbow joint, the tool comprising:
  a first guide tool comprising a boring guide aligned to create a bore in the distal humeral trochlea along a geometric axis of bend of the elbow joint when the first guide tool is engaged with the distal humeral trochlea;
  a first pin insertable through the bore in the distal humeral trochlea formed by the first guide tool, the first pin providing a physical reference corresponding to the geometric axis of bend;
  a second pin insertable into a humeral medullary canal generally along a diaphyseal axis of a humerus and generally normal to the first pin, the second pin providing a physical reference corresponding to the diaphyseal axis;
  a member determining a geometric relationship of the geometric axis of bend relative to the diaphyseal axis; and
  a cutting template engaged with at least the first pin and oriented to cut the distal humeral trochlea generally perpendicular to the geometric axis of bend.

20. A system for implanting a prosthesis in a distal humeral trochlea of an elbow joint, the tool comprising:
  a first guide tool comprising a boring guide aligned to create a bore in the distal humeral trochlea along a geometric axis of bend of the elbow joint, the first guide tool comprising first and second arms adapted to engage opposite sides of the distal humeral trochlea;
  a member coupled to the first arm and adapted to compressively engage the distal humeral trochlea, the member comprising a longitudinal channel with a central axis adapted to align with a geometric axis of bend of the elbow joint;
  a notch in the second arm shaped to engage an epitrochlea of a humerus and an orifice configured for alignment with the geometric axis of bend during engagement of the notch with the epitrochlea;
  a first pin insertable through the bore in the distal humeral trochlea formed by the first guide tool, the first pin providing a physical reference corresponding to the geometric axis of bend; and
  a cutting template engaged with at least the first pin and oriented to cut the distal humeral trochlea generally perpendicular to the geometric axis of bend.

* * * * *